(12) United States Patent
Hogrefe et al.

(10) Patent No.: US 6,320,041 B1
(45) Date of Patent: Nov. 20, 2001

(54) PRE-ACTIVATED CARBONYL LINKERS FOR THE MODIFICATION OF OLIGONUCLEOTIDES

(75) Inventors: Richard I. Hogrefe; Morteza M. Vaghefi, both of San Diego, CA (US)

(73) Assignee: Trilink Biotechnologies, Inc., San Diego, CA (US)

(*) Notice: Subject to any disclaimer, the term of this patent is extended or adjusted under 35 U.S.C. 154(b) by 0 days.

(21) Appl. No.: 09/834,828

(22) Filed: Apr. 13, 2001

(51) Int. Cl.[7] .......................... C07H 21/00; C07H 21/02; C07H 21/04

(52) U.S. Cl. .................. 536/25.3; 536/22.1; 536/23.1; 536/24.3; 536/24.33; 536/25.33; 536/25.34; 536/25.6; 536/26.1

(58) Field of Search .................. 536/22.1, 23.1, 536/24.3, 24.33, 25.3, 25.33, 25.34, 25.6, 26.1

*Primary Examiner*—Jezia Riley
(74) *Attorney, Agent, or Firm*—David B. Waller (57) ABSTRACT

The present invention provides a variety of compositions that comprise an activated carboxylic ester moiety on one end of an alkyl tether and a nucleic acid binding moiety on the other end for use as crosslinking reagents in conjugation reactions of nucleotides with solid support matrixes, organic molecules, reporter groups or other biomolecules.

25 Claims, 4 Drawing Sheets

PRE-ACTIVATED CARBONYL LINKERS FOR THE MODIFICATION OF OLIGONUCLEOTIDES

TECHNICAL FIELD

This invention relates to compositions utilized to chemically join two molecules of interest. More particularly, the compositions of the present invention are crosslinking reagents utilized to chemically join a desired molecule to an oligonucleotide.

BACKGROUND OF THE INVENTION

The preparation of oligonucleotide conjugates is generally accomplished through the use an oligonucleotide modified with a primary amine (Agrawal, S. (1994) Functionalization of oligonucleotides with amino groups and attachment of amino specific reporter groups. *Methods in Molecular Biology* 26; Protocols for Oligonucleotide Conjugates. (S. Agarwal, Ed.) pp. 73–92, Humana Press, Totowa, N.J. (Review), Meyers, R. (1994) Incorporation of Modified Bases into Oligonucleotides. *Methods in Molecular Biology* 26; Protocols for Oligonucleotide Conjugates. (S. Agarwal, Ed.) pp. 93–120, Humana Press, Totowa, N.J. (Review)). In most cases, amide or thiourea bonds are formed with conjugars containing an activated carboxyl or isothiocynate (ITC) functionality.

Although functionalization of many conjugars is routine, a number of conjugars have proved to be very difficult to transform into activated carboxyl or ITC derivatives either because of the complex synthesis involved or the inherent instability of the final compound. In an effort to circumvent these difficulties the coupling partners have been reversed placing the carboxylic acid function on the oligonucelotide, and the amine on the conjugar. The literature contains several examples of 5' terminal oligonucleotide linkers that contain a carboxyl funtionality. Unfortunately these methods have several disadvantages. Kremsky et al. ((1987) Immobilization of DNA via oligonucleotides containing and aldehyde or carboxylic acid group at the 5' terminus. *Nucleic Acids Research* 15, 2891–2909), describe conjugation with a protected 5' terminal oligonucleotide carboxyl group requiring cleavage of the methyl ester protecting group, followed by in situ activation with N-hydroxysuccinimide ("NHS") and a coupling reagent to achieve conjugation. The disadvantage of this method is the number of steps required to achieve the desired conjugate.

In another approach, the protecting group is a benzyl ester, which can be directly coupled to an amine (Endo, M., Gaga, Y., and Komiyama, M., (1994) A novel phosphoramidite for the site-selective introduction of functional groups into oligonucleotides via versatile tethers. *Tetrahedron Letter* 33, 3879–3882). However, this procedure calls for conditions that require treatment with a primary amine for 48 hours and is incompatible with base sensitive oligonucleotides, such as methylphosphonates (Hogrefe, R. I., Vaghefi, M. M., Reynolds, R. A., Young, K. M., and Arnold, L. J. Jr. (1993) Deprotection of methylphosphonate oligonucleotides using a novel one-pot procedure. *Nucleic Acids Research* 21, 2031–2038).

A third approach describes the formation of a phosphoramidate bond between a 3' or 5' phosphorylated oligonucleotide and an amino acid, followed by subsequent activation of the carboxyl moiety with carbodiimide (Gottikh, M., Asseline, U., and Thoung, N. T. (1990) Synthesis of oligonucleotides containing a carboxyl group at either their 5' end or their 3' end and their subsequent derivitization by an intercalating agent. *Tetrahedron Letters* 31, 6657–6660). The number of steps required to prepare these conjugates makes these methods generally undesirable.

Consequently there is a need for a fast and effective means of forming conjugating oligonucleotides to a variety of molecules while requiring a minimal amount of post-synthetic chemistry. In particular linker compositions are needed that may be synthesized from primary amine containing compounds that are relatively easy to obtain; comprise a non-labor intensive and efficient means for attachment to an oligonucleotide such as a phosphoramidite reagent that can be coupled directly to the 5' terminus; that are compatible with the conditions of oligonucleotide synthesis and that provide a highly reactive functionality, such as a succinimydyl or pentafluorophenyl ester. In addition, linker compositions that may be utilized in conjugations performed on support bound linker-modified oligonucleotides prior to deprotection and cleavage are particularly preferred.

SUMMARY OF THE INVENTION

The present invention relates generally to compositions of pre-activated linkers for the rapid modification of oligonucleotides.

In one aspect of the present invention a composition is provided of the formula, wherein
R$_1$ is R$_2$ is R$_3$ is —CH$_3$, —O—CH$_2$—CH$_2$—CN or —O—CH$_3$;
R$_4$ is o-chlorophenyl, β-cyanoethyl;
X$_1$ is O, S or Se; and
n is 5 to 15.

In another aspect of the invention a composition is provided of the formula, wherein
R₁ is R₂ is —CH₃, —O—CH₂—CH₂—CN or —O—CH₃;
X is O, S or Se; and
n is 5 to 15.

In one embodiment of this aspect the compositions above further comprising a nucleic acid, preferably a nucleic acid from 1 to 1,000 nucleotides in length, a nucleotide bound to a support matrix or a solid support matrix.

In yet another aspect of the invention a composition is provided comprising a nucleoside from 1 to 1,000 nucleotides in length conjugated to a reporter group utilizing the compositions above, wherein said reporter group is selected from the group consisting of fluorescent, bioluminescent, chemiluminscent, colorimetric and radioactive agents. In particular, when the reporter group is a fluorescent reporter group it may be selected from the group consisting of fluorescein, pyrene, 7-methoxycoumarin, Cascade Blue™, 7-aminocoumarin ("AMCA-X"), dialkylaminocoumarin, Pacific Blue, Marina Blue, BODIPY 493/503™, BODIPY Fl-X™, (4,6-dichlorotriainyl)aminofluorescien) ("DTAF"), Oregon Green 500™, 6-((5-dimethylaminonaphthalene-1-sulfonyl)amino)hexanoate ("Dansyl-X"), 6-(fluorescein-6-carboxamido)hexylamine ("6-FAM"), Oregon Green 488™, Oregon Green 514™, Rhodamine Green-X™, Rhodol Green™, NBD, Tetrachlorofluorescein ("TET"), 2', 4', 5', 7'tetrabromosulfonefluorescien, BODIPY-R6G™, BODIPY-Fl Br₂™, BODIPY 530/550™, hexachlorofluorescein ("HEX"), BODIPY 558/568™, BODIPY-TMR-X™, 1-(3-carboxybenzyl)-4-(5-(4-methoxyphenyl)oxazol-2yl) pyridinium bromide ("PyMPO"), BODIPY 564/570™, 6-(tetramethylrhodamine-5(6)-carboxamido)hexylamine ("TAMRA"), Cy3™, Rhodamine Red-X™, BODIPY 576/589™, CarboxyXrhodamine™, BODIPY 581/591™, Texas Red-X, BODIPY-TR™, Cy5™, and naphthofluorescein.

In one embodiment of this aspect the nucleic acid may be a deoxynucleotide or a ribonucleotide or a combination of DNA and RNA. In another embodiment a first nucleic acid may be conjugated to a second nucleic acid wherein the first nucleic acid is from 1 to 1,000 nucleotides in length and the second nucleic acid is from 1 to 1,000 nucleotides utilizing the composition above.

In yet another embodiment of this invention a composition is provided comprising a nucleic acid from 1 to 1,000 nucleotides in length conjugated to a biomolecule or an organic molecule utilizing the composition.

In still another aspect of the invention the following compounds are provided:

DEFINITIONS

The terms "alkyl moiety", "alkyl tether" or "tether" as referred to in the present invention may be a saturated or unsaturated, straight or branched chain, or substituted or unsubstituted alkyl chain of carbon atoms. Preferably, the alkyl moiety is from about 2 to about 25 carbon atoms in length, more preferably the alkyl moiety is a straight chain unsaturated, unsubstituted and from about 3 to about 15 carbon atoms in length and most preferably from about 7 to about 11 carbon atoms in length.

The terms "activated carboxylic ester moiety" or "activated ester" as referred to in the present invention is a moiety that is reactive with amine groups present on a target molecule to be conjugated utilizing the compounds of the present invention.

The term "nucleic acid binding moiety" as referred to in the present invention is a group that is reactive with a hydroxy group of a nucleoside, nucleotide or oligonucleotide to be conjugated utilizing the compounds of the present invention under acidic conditions.

DETAILED DESCRIPTION OF THE INVENTION

The compositions of the present invention comprise an activated carboxylic ester moiety, an alkyl tether and a nucleic acid binding moiety. The activated carboxylic ester moiety may be any moiety that interacts with a primary or secondary amine of a target molecule to form an amide bond. The activated ester may be selected from a variety of moieties known to those skilled in the art such as for example a succinamidyl moiety, a pentafluorophenyl moiety, a phthalimide moiety, a dinitrophenyl moiety, a benztriazole moiety or other similar moiety. When the activated ester is to be utilized to bind a target molecule such as a protein for example an enzyme or an organic molecule for example fluoresceinamine the reaction is conducted under basic conditions. Under these conditions the reaction between a free amine of the target molecule with the formation of an amide bond is favored over the reaction of a free amine with the nucleic acid binding moiety of the linker.

The alkyl tether may be comprised of a variety of alkyl moieties that provide the desired length between the activated carboxylic ester moiety and the nucleic acid binding moiety that is stable under conjugation reaction and oligonucleotide synthesis conditions, does not interfere with desired conjugation or synthesis reactions and does not substantially interact with reactive groups that may be present on the target molecule. The terms substantially means that while the alkyl tether may interact with reactive groups present on the target molecule it will not compete or interfere with the desired reaction of the activated carboxylic ester moiety with the target molecule or the nucleic acid binding moiety of the linker with the nucleic acid molecule. The alkyl tether may be a straight or branched chain, saturated or unsaturated, substituted or unsubstituted and may be about 5 to about 25 carbon atoms in length. Preferably the alkyl moiety is an unsubstituted saturated straight chain of about 7 to about 11 carbon atoms in length.

The nucleic acid binding moiety is a moiety that interacts with a hydroxyl group of a nucleic acid to form a phosphodiester bond. Preferably the hydroxyl group is the 5' hydroxyl of the nucleic acid molecule. The nucleic acid binding moiety may be selected from a variety of moieties known to those skilled in the art that are able to interact with the hydroxyl of a nucleic acid molecule. Preferably the nucleic acid binding moiety is a phosphoramidite, a methylphosphoramidite, or a H phosphonate triethylammonium salt. When the nucleic acid binding moiety is to be utilized to bind a hydroxyl group of a nucleotide such as the 5' hydroxy the reaction is conducted under acidic conditions.

Figure 1:
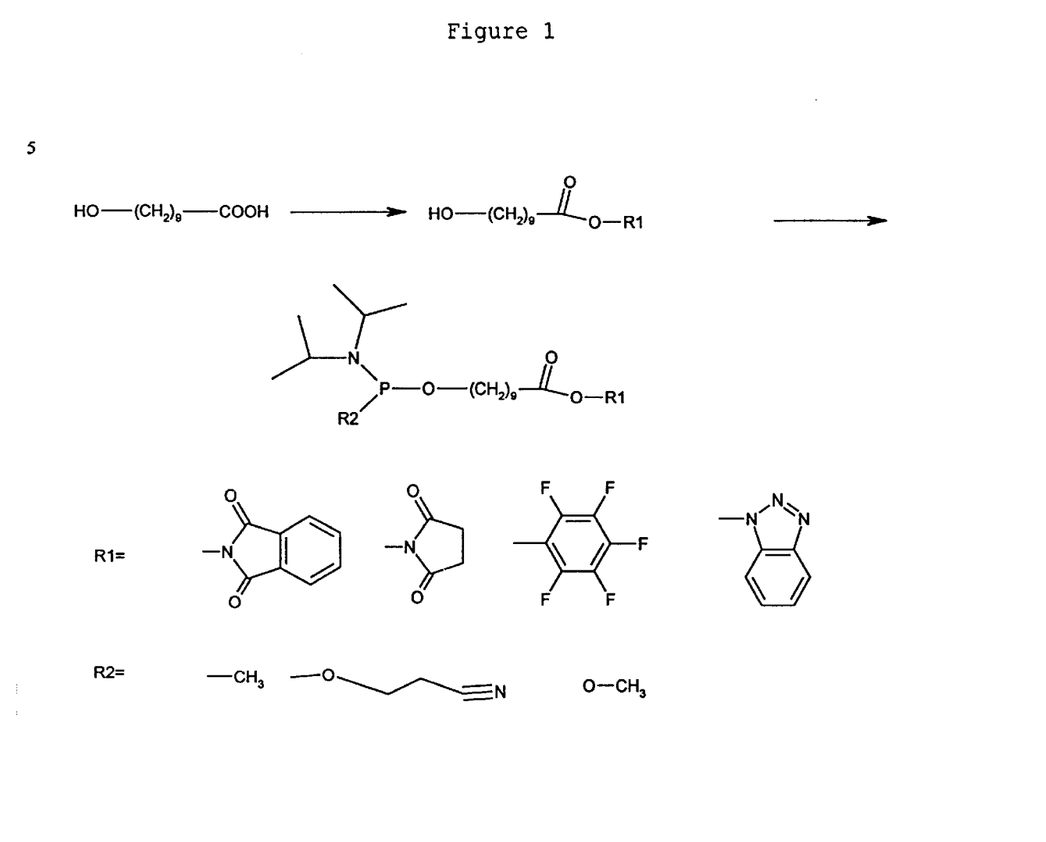
FIG. 1. Synthetic scheme for the preparation of succinimidyl 10-(N,N-diisopropylmethylphosphonamidyl)-decanoate (DAMP).

While the linkers of the present invention may be prepared from a variety of esters. 10-hydroxydecanoic acid ester was utilized in the examples by way of illustration and not by way of limitation (see FIG. 1). Synthesis yields for these esters ranged from about 30 to about 95%.

The coupling of linkers to oligonucleotides may be performed by first dissolving linker amidites in anhydrous acetonitrile to a concentration of 0.1 M. These were stored over molecular seives (3 Å) overnight prior to use. The acetonitrile and 0.45M tretrazole reagent obtained from Glen Research Corporation, (Sterling, Va.) were tested by Karl-Fisher titration just prior to use to ensure that they contained less than 30 ppm water. The linkers were then coupled using the following manual method (1 μmole scale), the support was first detritylated by slowing passing through 5 ml of 2.5% dichloroacetic acid in dichloromethane. When no more trityl was observed (approximately 1.0 minute), the column was washed with 30 ml of anhydrous (<30 ppm H$_2$O) acetonitrile using a syringe. The linker (20 eq.; 200 μL) was drawn into a 1.0 mL syringe. The activator (0.45 M tetrazole in acetonitrile, 200 μL, 4.5 eq. over amidite) was drawn into another 1.0 mL syringe. The syringes were placed on opposite ends of the column and the reagent passed back and forth for exactly 1.0 minute, at which time the reagent (slightly discolored brown) was completely drawn into a syringe.

The phosphonite intermediate was then oxidized immediately using (1S)-(+)-(10-camphorsulfonyl)oxaziridine (0.1 M in acetonitrile; 2 ml), which was passed back and forth through the column using the two syringe method for 1.0 minute as described in the preceeding paragraph. The column was washed with 20 mL of acetonitrile, then dried with a stream of argon gas prior to removal of the support from the column.

The crude product was purified on a Water (Milford, Me.) μBondapak C-18 reverse phase column (4.6×305 mm) using a gradient of acetonitrile (5% to 70% over 70 minutes) in 100 mM triethylamminoium hydroxide, pH 7, at a flow rate of 1 mL/minute. The purified product was then quantitated.

As stated above the activated carboxylic ester may bind a variety of target molecules having a free amine, preferably a primary or secondary amine. Target molecules include biomolecules such as proteins, for example antibodies or enzymes, nucleic acids comprising at least one base having a free amine or that has been modified to comprise a free amine and organic molecules such as fluoroscein.

The biomolecules maybe proteins of a therapeutic nature, such as for example those that stimulate, activate or repress a biological process, that act to target or isolate the conjugar, such as an antibody, it may be a reporter group such as an enzyme for example alkaline phosphatase, horseradish peroxidase or glucose oxidase or it may be a nucleic acid comprising at least one base that has been modified to contain a free amine. One skilled in the art would recognize that a wide variety of biomolecules that may perform a number of different functions, including for example biological, therapeutic or diagnostic, and that have a primary or secondary amine that will bind the activated carboxylic ester of the linker may be utilized with the present invention based on the needs of the user.

Correspondingly a larger number of organic molecules of a therapeutic nature, such as those that stimulate, activate or repress a biological process for example antibiotics, that act to target or isolate the conjugar, such as biotin modified to contain a free amine, or that function as a reporter group such as a fluorescent molecule for example fluorescein. If the molecule is an antibiotic it may be selected from those antibiotics having a free primary or secondary amine listed for example in the Dictionary of Antibiotics and Related Substances edited by Bycroft, Chapman and Hall 1988. The antibiotics having a free amine include for example any aminoglycoside such as glucosamine or galactosamine, an antibiotic molecule which contains an aminoglycoside such as neomycin or a peptide antibiotic that contains arginine or diaminobutyric acid.

If the molecule is a fluorescent it is preferably fluorescein, pyrene, 7-methoxycoumarin, Cascade Blue™, 7-aminocoumarin ("AMCA-X"), dialkylaminocoumarin, Pacific Blue, Marina Blue, BODIPY 493/503™, BODIPY Fl-X™, (4,6-dichlorotriainyl)aminofluorescien) ("DTAF"), Oregon Green 500™, 6-((5-dimethylaminonaphthalene-1-sulfonyl)amino)hexanoate ("Dansyl-X"), 6-(fluorescein-6-carboxamido)hexylamine ("6-FAM"), Oregon Green 488™, Oregon Green 514™, Rhodamine Green-X™, Rhodol Green™, NBD, Tetrachlorofluorescein ("TET"), 2', 4', 5', 7'tetrabromosulfonefluorescien, BODIPY-R6G™, BODIPY-Fl Br$_2$™, BODIPY 530/550™, hexachlorofluorescein ("HEX"), BODIPY 558/568™, BODIPY-TMR-X™, 1-(3-carboxybenzyl)-4-(5-(4-methoxyphenyl)oxazol-2yl) pyridinium bromide ("PyMPO"), BODIPY 564/570™, 6-(tetramethylrhodamine-5(6)-carboxamido)hexylamine ("TAMRA"), Cy3™, Rhodamine Red-X™, BODIPY 576/589™, CarboxyXrhodamine™, BODIPY 581/591™, Texas Red-X, BODIPY-TR™, Cy5™, and naphthofluorescein or other molecules that have a free amine and are listed in for example Catalog Molecular Probes: Handbook of fluorescent probes and research chemicals by R. P. Haugland 6$^{th}$ Ed. 1996, specifically chapter 6.

In addition, nucleic acids such as for example nucleotides, polynucleotides or oligonucleotides constructed of DNA, RNA or a combination of both comprising at least one base having a free amine or modified to contain at least one amine may also form an amide bond with the linker of the present invention. Preferably the nucleic acid is from 1 to 1,000 nucleotides in length, more preferably from 5 to 500 nucleotides in length and most preferably from 10 to 150 nucleotides in length.

In the case of phosphrothioate oligonucleotide conjugates, the entire process of linker coupling, conjugation and deprotection can be accomplished in one day.

These novel linkers have several advantageous properties.
1. The reagent is readily made in two steps and is relatively inexpensive. Since the reagent is an amidite, it is readily adaptable to automated synthesis. Applicants' have successfully coupled two week old solutions of the reagent stored over molecular seives in the refrigerator. Lots stored as dried oils in the freezer have been stable for more than six months.
2. Because the activated carboxyl is part of the linker, the user is able to use amine derivitized conjugars rather than isothiocyanates. The advantages to this are multi-fold. First, Applicants have observed that amines are much easier synthetic targets in many instances for a variety of reasons and more potential conjugars are available commercially as amines than as activated carboxyls. Secondly, the conjugar is not hydrolyzed during the reaction and is able to be utilized in the next conjugation reaction without further manipulation.
3. The chemistry of the present invention may be entirely accomplished on solid support, with the advantages inherent with that technology. It is preferable that fast deprotecting bases and ethylenediamine conditions generally be used for oligonucleotide synthesis. The deprotection method is generally complete within 6 hours and is compatible with phosphodiester and phosphorothioate chemistries. It is preferable that a labile protection group is used for cytidine, such as isobutyryl, to prevent transamination products when using ethylenediamine.

EXAMPLES

Nucleoside methylphosphonamidites were obtained from JBL Scientific, Inc. (San Luis Obispo, Calif.). All other oligonucleotide synthesis reagents were obtained from Glen Research Corporation (Sterling, Va.) or prepared as previously described (5, 8). Oligonucleotide synthesis was done on a Perseptive (Novo, Calif.) Expedite 8900 DNA synthesizer using previously described methods in the case of the chimeric oligonucleotide Hogrefe, R. I. Reynolds, M. A., Vaghefi, M. M., Young, K. M., Riley, T. A., Klem, R. E., and Arnold, L. J. Jr. (1993) An improved method for the synthesis and deprotection of methylphosphonate oligonucleotides. *Methods in Molecular Biology.* 20; Protocols for Oligonucleotides and Analogs. (S. Agarwal, Ed.) pp. 143–164, Humana Press, Totowa, N.Y.) and manufacturer supplied methods in the case of the phosphorothioate.

Solvents were obtained from Fisher Scientific, Inc. (Pittsburgh, Pa.). All other reagents, except as noted, were obtained from Aldrich Chemical Co., Inc. (Milwaukee, Wis.).

HPLC was accomplished on a Beckman, Inc. (Fullerton, Calif.) System Gold Model 126 with Model 168 photodiode array detector. UV absorbances were obtained on a Model 3000 Photodiode Array Spectrophotometer from Milton Roy Company (Rochester, N.Y.). NMR was obtained on a Bruker Model ARX 300 spectrometer. Electrospray and FAB mass spectroscopy analysis were done by the analytical service dept. of Scripps Research Institute (San Diego, Calif.).

Example 1

Preparation of Pentafluorophenyl 10-hydroxydecanoate

The 10-hydroxydecanoic acid (4.5 g, 23.9 mmole) was dried by co-evaporation with anhydrous pyridine twice. The residue was dissolved in anhydrous pyridine (100 mL) and triethylsilyl chloride (5.6 mL, 33.5 mmole) was added to the stirring solution at room temperature. Completion of the reaction was observed at 30 minutes by silica gel tlc (ethyl actetate, acetic acid (AcOH), heptane; 16%/1%/83%; $R_f$ 0.31). The solvent was evaporated in vacuo. The product was carried on to the next reaction without purification. Crude triethylsilyl protected 10-hydroxydecanoic acid was dissolved in dichloromethane (20 mL) and chilled in an ice bath. Triethylamine (4.0 mL, 28.7 mmole) was added followed by the slow addition of pentafluorophenyl trifluoroacetate (2.7 mL, 15.9 mmole). The reaction was determined complete at 3 hours by silica gel tlc (ethyl actetate, acetic acid, heptane; 16%/1%/83%; $R_f$=0.80). The solvent was evaporated in vacuo. The hydroxyl was deprotected in 30 minutes with THF:AcOH:H$_2$O (34 mL, 8:8:1), as observed by silica gel tlc (ethyl acetate, acetic acid, heptane; 16%/1%/83%; $R_f$ 0.20). The mixture was evaporated to dryness. The crude product was purified by column chromatography (200 g EM Science silica gel 60 230–400 mesh; 10% ethyl actetate, 1% AcOH, heptane) yielding 2.6 g (30.7%). $^1$H NMR (CDDl$_3$): δ3.65 (t, 2H, J=6.59 Hz), 2.66 (t, 2H, J=7.41 Hz), 1.82–1.72 (m, 2H), 1.60–1.53 (m, 2H), 1.41–1.31 (m, 10H). Mass spectrum (FAB$^+$), m/z 355 (MH$^+$).

Example 2

Preparation of Pentafluorophenyl 10-(N,N-diisopropylmethylphosphonamidyl)-decanoate Pentafluorophenyl 10-hydroxydecanoate (0.9 g, 2.54 mmole) was dissolved in anhydrous dichloromethane (30 mLs) under argon. Diisopropylethylamine (580 uL, 3.3 mmole) was slowly added to the reaction mixture followed by the dropwise addition of chloromethyl-N,N-diisopropylaminophosphine while stirring at room temperature. The reaction was determined complete at 35 minutes by silica gel tlc (ethyl actetate, triethylamine, heptane; 15%/1%/84%; $R_f$ 0.56) using a plate that was pretreated with the triethyamine containing solvent to minimize hydrolysis of the product. The solvent was evaporated in vacuo and the crude product was immediately purified by column chromatography using the same eluent as described for the tlc (30 g EM Science Silica gel 60 230–400 mesh, pretreated with the eluent). The product fractions were evaporated yielding 860 mgs of clear oil (67.8% yield). $^1$H NMR (CDCl$_3$): δ3.58–3.47 (m, 4H), 2.65 (t, 2H, J=7.41 Hz), 1.79–1.74 (m, 2H), 1.55–1.54 (m, 2H), 1.40–1.31 (m, 10H), 1.20 (s, 3H), 1.17 (d, 6H, J=6.32 HZ), 1.10 (d, 6H, J=6.75 Hz). $^{31}$P NMR (CDCl$_3$): δ114.41 (s) referenced with external PO(OH)$_3$ in D$_2$O. Mass spectrum (FAB$^+$), m/z 500 (MH$^+$).

Example 3

Preparation of Succinimidyl 10-hydroxydecanoate

To a solution of 10-hydroxydecanoic acid (10 g, 53 mmol) in dioxane (200 mL) at room temperature was added N-hydroxysuccinimide (NHS) (6.12 g, 53 mmol) followed by N, N'-dicyclohexylcarbodiimide (DCC) (11.4 g, 53 mmol). Quantitative conversion to product was achieved after stirring at room temperature for 45 minutes as determined by tlc using silica gel (ethyl acetate/heptane 4:1; $R_f$=0.28). The precipitate was removed by filtration, and the solvent was removed in vacuo. The resulting solid was taken up in ethyl acetate (250 mL), and the remaining dicyclohexylurea was removed by filtration. The organic layer was washed with 5% NaHCO$_3$ (twice with 60 mL), brine (60 mL), dried over anhydrous MgSO$_4$, filtered and concentrated in vacuo, to afford 14.23 g (94%) of the desired succinimidyl ester. The product was carried on to the next step without purification. $^1$H-NMR (CDCl$_3$): δ3.46 (t, 2H, J=7 Hz), 2.75 (s, 4H), 2.59 (t, 2H, J=7 Hz), 1.62–1.72 (m, 2H), 1.29–1.47 (s+m, 12H ). Mass spectrum (FAB$^+$), m/z 286 MH$^+$).

Example 4

Preparation of Succinimidyl 10-(N, N-diisopropyl methylphosphonamidyl)-decanoate Succinimidyl 10-hydroxydecanoate (0.750 g, 2.6 mmol) was dissolved in anhydrous dichloromethane (20 mL). Triethylamine (0.720 mL, 5.2 mmol) was added via syringe at room temperature followed by chloromethyl-N,N-diisopropylaminophosphine (CI-MAP) (0.70 mL, 3.4 mmol). The reaction was followed by tlc using silica gel plates pretreated as described above (ethyl acetate/heptane 1:1 with 1% triethylamine; $R_f$=0.40). Near quantitative conversion to product was observed after stirring for 20 minutes at room temperature. The organic layer was washed with 5% NaHCO$_3$ (twice with 5 mL), dried over Na$_2$SO$_4$, and concentrated in vacuo, to afford (1.12 g) of a crude transparent oil which was immediately loaded on to a column (1½ inch×16 inch) of silica (30 g; EM Science Silica gel 60 230–400 mesh) pre-treated with the running eluent (ethyl acetate/heptane 1:1 with 1% triethylamine). After pooling and concentration of the desired fractions, 0.719 g (64%) of the product was obtained. $^1$H-NMR (CD$_3$-CN): δ3.47–3.58 (m, 4H), 2.83 (s, 4H), 2.59 (t, J=7 Hz), 1.69–1.79 (m, 2H), 1.25–1.37 (s+m, 12H), 1.18 (d,J=8 Hz), 1.18 (d, J=7 Hz), 1.09 (d, J=7 Hz). $^{31}$P-NMR (CD$_3$-CN): δ119.09, referenced with external PO(OH)$_3$ in D$_2$O. Mass spectrum (FAB$^+$), m/z 431 (MH$^+$).

Example 5

Preparation of Succinimidyl 10-(2-cyanoethyl-N,N'-diisopropylphosphororamidyl)-decanoate Succinimydyl 10-hydroxydecanoic acid (3.7 g; 13.0 mmole) was dissolved in 100 mL of anhydrous dichloromethane. The reaction flask was then cooled to 0° C. and 3.40 mL (1.5 eq, 19.5 mmole) of diisopropylethylamine added, followed by 3.48 mL (1.2 eq, 15.6 mmole) of 2-cyanoethyl-N,N'-diisopropylchlorophosphoramidite. This was allowed to stir at room temperature for 50 minutes at which time the reaction was shown complete by silica tlc (2:1 ethyl acetate/heptane with 0.5 triethylamine) and the solvent evaporated. Purification was done by flash silica gel eluent, ethyl acetate/heptane 1:1 with 1% triethylamine, yielding 1.7 g; 27%, of pure product. $^1$H-NMR (CD$_3$-CN) δ3.8 (m, 2H), 3.6 (m, 4H), 2.8 (s, 4H), 2.6 (m, 4H), 1.7 (m, 2H), 1.5 (m, 2H), 1.2 (s, 10H), 1.1 (d, 2H). 31P-NMR (CD$_3$-CN) δ147 ppm referenced with external PO(OH)$_3$ in D$_2$O. Electrospray mass spectral analysis: 486 au.

Example 6

Preparation of Phthalimidyl 10-hydroxydecanoate

To a solution of 10-hydroxydecanoic acid (1.880 g, 10 mmol) in dichloromethane (25 mL) at room temperature was added N-hydroxyphthalimide (NHP) (1.63 g, 10 mmol) followed by N, N'-dicyclohexylcarbodiimide (DCC) (2.1 g, 10 mmol). Quantitative conversion to product was achieved after stirring at room temperature for 45 minutes as determined by tlc using silica gel (ethyl acetate/heptane 4:1;

Example 7

Preparation of Phthalimidyl 10-(2-cyanoethyl-N,N'-diisopropylphosphoramidyl)-decanoate Phthalimydyl 10-hydroxydecanoic acid (1.7 g, 5.1 mmole) was dissolved in 30 mL of anhydrous dichloromethane. To the reaction mixture diisopropylethylammonium tetrazolide (0.43 g, 2.5 mmole) and 2-cyanoethyl-N,N',N'',N'''-tetraisopropylphosphoramidite (1.54 g 5.1 mmole) was added. This was allowed to stir at room temperature for 2 hours at which time the reaction was shown complete by silica tlc (2:1 ethyl acetate/heptane with 0.5 triethylamine) and the solvent evaporated. Purification was done by flash silica gel eluent, ethyl acetate/heptane 1:1 with 1% triethylamine, yielding 1.4 g; 52%, of pure product. $^1$H-NMR (CD$_3$CN) $\delta$7.89 (m, ar), 3.8 (m, 2H), 3.6 (m, 4H), 2.8 (s, 4H), 2.6 (m, 4H), 1.7 (m, 2H), 1.5 (m, 2H), 1.17 (s, 10H), 1.1 (d, 2H). 31P-NMR (CD$_3$-CN) $\delta$148 ppm referenced with external PO(OH)$_3$ in D$_2$O.

Example 8

Conjugation of fluorescein cadaverene (5-((5-aminopentyl)-thioureidyl)fluorescein) to a chimeric oligonucleotide using

DAMP

The following procedure was used with both the succinimidyl and PFP DAMP linkers: Fluorescein cadaverene (eqs.; 2 mg; 4 $\mu$mole) was dissolved in a solvent mixture containing dimethylformamide (0.25 mL); water (0.15 mL), and 1 M aqueous HEPES buffer, pH 8 (0.1 mL) in a 1 mL autosampler glass vial. The support-bound oligonucleotide with the DAMP linker (1 $\mu$mole) was added to this reagent and the reaction mixed 4 hours at room temperature using a rotary mixing wheel. At that time, excess fluorescein cadaverene was decanted from the reaction, and the beads washed well with 1:1 acetonitrile/water until no fluorescence was noted in the wash.

The oligonucleotide was deprotected and desalted on a reverse-phase cartridge using previously described methods (5). The crude material (90 OD succ; 94 Ods—PFP) was analyzed and an aliqout purified for mass spectral analysis on a reverse-phase Waters (Millford, Me.) $\mu$Bondapak C-18 column with a gradient of acetonitrile (0–50% over 50 minutes) in 0.1 M triethylammonium acetate (TEAA), pH 7. The product was retained on the column, eluting 7 minutes after the starting oligonucleotide as a doublet. Independent isolation of each peak of the doublet yielded compound with the same correct mass (6670 amu) as determined by electrospray mass spectroscopy.

The succinimidyl version of the linker yielded 34% product, as determined by the integrated area of the 260 nm chromatogram of the crude product mixture. The PFP ester analog yielded 22% product.

Example 9

Conjugation of Octadecylamine to a Phosphorothioate Oligonucleotide using DADE-SE The octadecylamine was conjugated to a phosphorothioate of mixed base sequence 18 nucleotides in length. The linker was coupled to the CPG bound oligonucleotide as described in Example 8 above for DAMP, with the exception that the CSO was replaced with 10 eq. of Beaucage reagent (0.1 M in acetonitrile, 3 minutes at room temperature). The scale of the synthesis was 5 $\mu$mole, thus requiring 1 mL of the linker and tetrazole reagents to achieve 20 molar equivalent excess. All other reagents and washes were merely doubled.

After the linker modified support-bound oligonucleotide was washed and dried, the beads were added to a vial containing 10 eq. of 1-octadecylamine (stearylamine) dissolved in 2 mL of dichloromethane with 10% triethylamine. The reaction was allowed 4 hours at room temperature with continuous mixing. The beads were then washed well with dichloromethane and dried.

The oligonucleotide conjugate was then deprotected and cleaved from support using 2 mL of conc. ammonium hydroxide for 5 hours at 65° C., after which time the reagent was decanted and the beads rinsed with 4 mL of 25% acetonitrile in water. The combined solutions were dried in vacuo. The resulting residue was reconstituted in 1 mL of 25% acetonitrile in water and the yield determined (965 OD$_{260}$ units).

The crude product was analyzed and purified on a Water (Milford, Me.) $\mu$Bondapak C-18 reverse phase column (4.6× 305 mm) using a gradient of acetonitrile (5% to 70% over 70 minutes) in 100 mM triethylamminoium acetate, pH 7, at a flow rate of 1 mL/minute. The product was isolated (435 OD$_{260}$ units; 45%) using the same system and injecting 200 OD$_{260}$ units of the crude sample per run. The isolated oligonucleotide conjugate was analyzed by electrospray mass spectroscopy and found to have the correct mass (6585 au).

Example 10

Conjugation of Fluorescien-cadaverene to a Phosphorothioate Oligonucleotide using DADE-PE The fluorescien-cadaverene was conjugated to a phosphorothioate of mixed base sequence 18 nucleosides in length. The linker was coupled to the CPG bound oligonucleotide as described in Example 8 above for DAMP, with the exception that the CSO was replaced with 10 equivalents of Beaucage reagent, 0.1 M in acetonitrile, 3 minutes at room temperature. The scale of the synthesis was 1 $\mu$mole, thus requiring 1 mL of the linker and tetrazole reagents to achieve 20 molar equivalent excess. All other reagents and washes were doubled.

After the linker modified support-bound oligonucleotide was washed and dried, a 10 eq. of fluorescien-cadaverene dissolved in 1 mL of dimethlformamide with 10% triethylamine was pushed back and force into the synthesis column. The reaction was allowed 1 hour at room temperature with occasional mixing. The beads were then washed well with dichloromethane and dried.

The oligonucleotide conjugate was then deprotected and cleaved from support using 2 mL of conc. ammonium hydroxide for 18 hours at 55° C., after which time the reagent was decanted and the beads rinsed with 4 mL of 25% acetonitrile in water. The combined solutions were dried in vacuo. The resulting residue was reconstituted in 1 mL of 25% acetonitrile in water and the yield determined.

The crude product was analyzed on a PAGE gel and quantified on a Water (Milford, Me.) μBondapak C-18 reverse phase column (4.6×305 mm) using a gradient of acetonitrile (5% to 70% over 70 minutes) in 100 mM triethylamminoium acetate, pH 7, at a flow rate of 1 mL/minute. The chromatogram was analyzed for quantitation.

Examples 11

Comparison of the Conjugation Efficiency of the MAMP-PFPE and DAMP-SE Versions of the DAMP Linker We tested the conjugation efficiency of the two linkers using fluorescein cadaverene (5-((5-aminopentyl)-thioureidyl)fluorescein) as the conjugar. The oligonucleotide (24 mer) was a chimeric compound containing methylphosphonate linkages near the 3' and 5' ends of the oligonucleotide alternating with phosphodiester linkages and containing an internal core of four phosphorothioate linkages centrally positioned (a) This type of alternating construct is described by Reynolds, M. A., Hogrefe, R. I., Jaeger, J. A., Schwartz, D. A., Riley, T. A., Marvin, W. B., Daily, W. J., Vaghefi, M. M., Beck, T. A., Knowles, S. K., Klem, R. E., Arnold, L. J. Jr. (1996) Synthesis and thermodynamics of oligonucleotides containing chirally pure $R_p$ methylphosphonate linkages; *Nucleic Acids Research* 24. 4584–4591 (b) The specific sequence is being held confidential by Genta.

Figure 2:
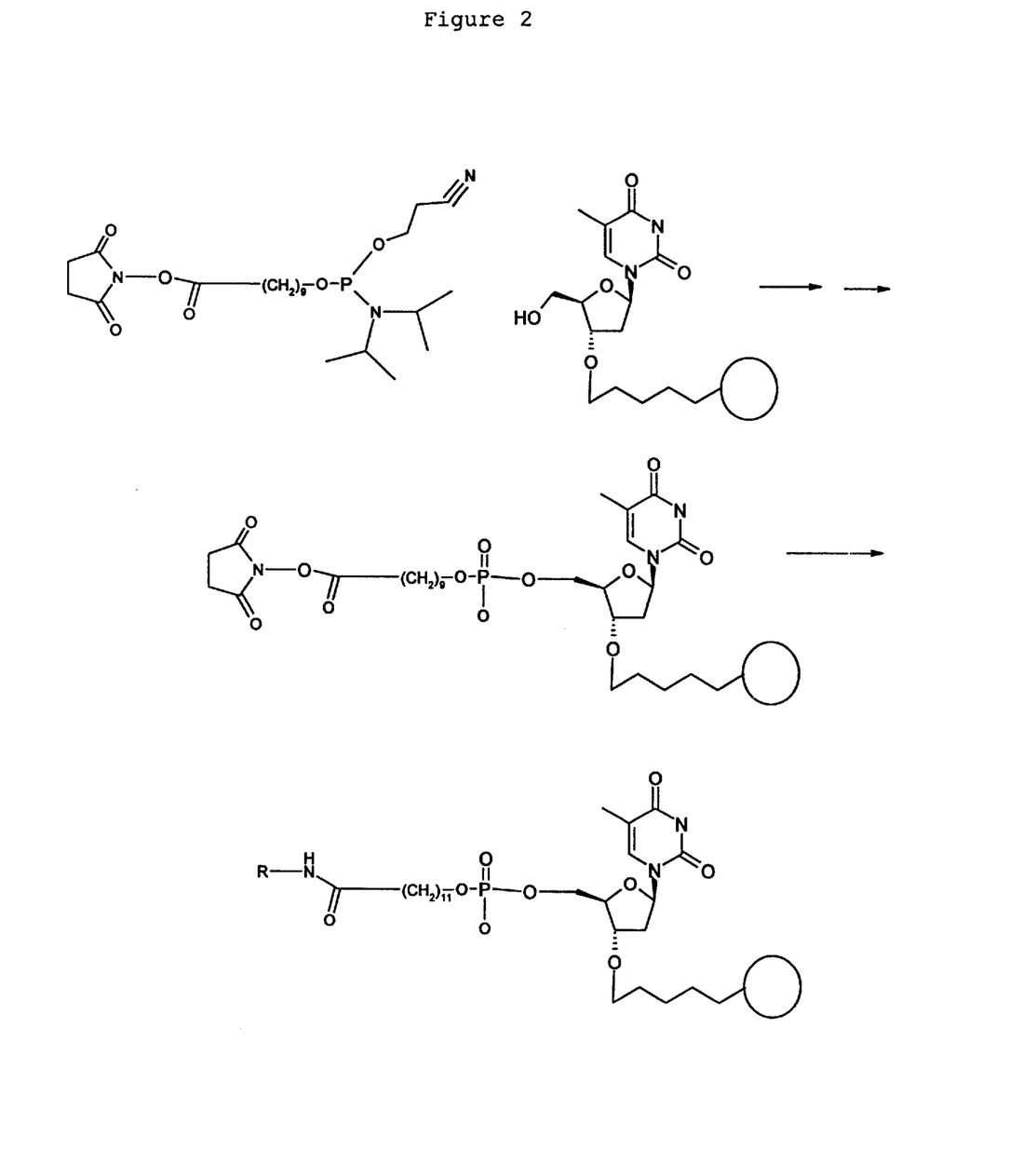
FIG. 2. Coupling and conjugation scheme for the modification of oligonucleotides using DAMP or succinimidyl 10-(2-cyanoethyl-N, N'-diisopropylphosphoramidyl)-decanoate (DADE).

FIG. 2 illustrates the solid phase conjugation scheme used with the activated acid linkers. The coupling of the linker to the support-bound oligonucleotide was accomplished manually as described above in the examples. To ensure comparability, 1 μmole aliqouts of support were removed from a common 15 μmole scale oligonucleotide synthesis. The support bound oligonucleotide was loaded into 1 μmole scale synthesis columns.

The linkers were dissolved the previous day to a concentration of 0.1 M in dry acetonitrile. We then added 3 A molecular seives to ensure dryness of the reagent. This is even more crucial in the case of methylphosphonamidite reagents than standard phosphoramidites. The phosphonite intermediate was oxidized with (1S)-(+)-(10-camphorsulfonyl)oxaziridine (CSO); 0.1 M in acetonitrile, for 1 minute. We chose CSO as the oxidant because the reagent does not require a base or water, as does the commonly used iodine. Our observation is that CSO generally yields a cleaner product, as determined in dinucleotide experiments, nmr studies, and a direct comparison with this linker (data not shown).

Figure 3:
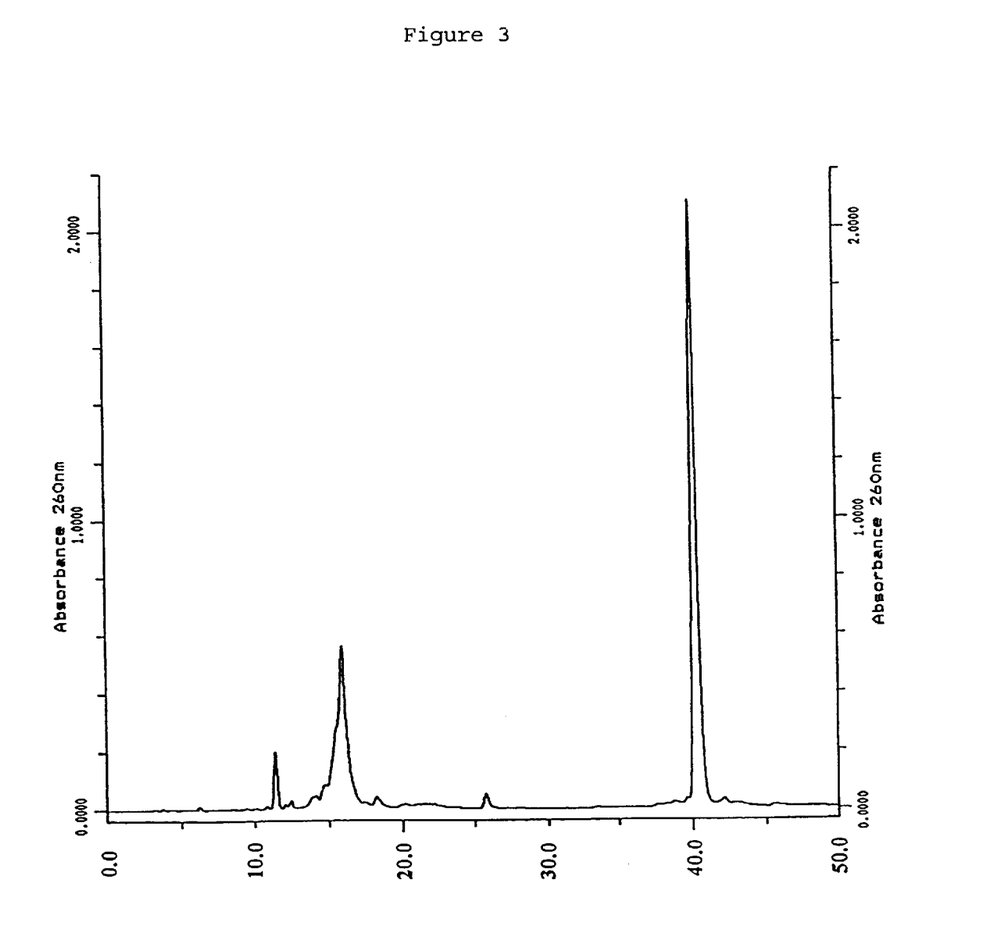
FIG. 3. Rate of conjugation of DADE modified phosphqrothioate oligonucleotide with octadecylamine.

The fluorescein cadaverene was conjugated to the functionalized oligonucleotide by dissolving 4 equivalents of the conjugar in 9:1 dimethylformamide/aqueous HEPES buffer, pH 8. The support was added to this reagent and the reaction mixed overnight at room temperature using a rotary mixing wheel. (A subsequent time course experiment demonstrated that 4 hours at room temperature is sufficient for completion of the conjugation reaction with unhindered primary amines. (FIG. 3) At that time, excess fluorescein cadaverene was decanted from the reaction, and the beads washed well with 1:1 acetonitrile/water until no more fluorescence was noted in the wash. The excess reagent was stored for use in subsequent reactions, since the conjugar is stable and not hydrolyzed, in contrast to traditional carboxyl activated conjugars which are discarded after use.

The methyphosphonate containing oligonucleotide was then deprotected using the one-pot ethylenediamine method described earlier. The crude material was analyzed and purified on a reverse-phase Waters μBondapak C-18 column with a gradient of acetonitrile in 0.1 M triethylammonium acetate, pH 7. The product was retained on the column, eluting approximately 7 minutes after the staring oligonucleotide as a doublet. (Methylphosphonate oligonucleotides with a 5' modification will occasionally split into two diasteriosomers. The identity of each peak was verified by independent isolation and mass spectral analysis. The peaks had identical uv spectra as well.

The succinimidyl version of the linker yielded 34% product, as determined by the integrated area of the 260 nm chromatogram of the crude product mixture. Based on the area of the remaining starting oligonucleotide and compared to a standard unconjugated crude oligonucleotide mixture obtained by deprotection of a portion of the same support, the coupling and conjugation occurred with an overall efficiency of approximately 75% combined.

The pfp ester version of the linker yielded 22% product, with an overall efficiency of 60%. In both cases the efficiency of conjugation step alone appeared to be better than 80%.

Example 12

Use of DADE-SE to Prepare a Lipophilic Conjugate of a Phosphorothioate Oligonucleotide The utility of the DADE-SE version of the linker (as the succinimidyl ester) was demonstrated by the preparation of an octadecylalkyl conjugate to 4.6 μmole of phosphorothioate oligodeoxynucleotide. The DADE linker was coupled to the support-bound phosphorothioate oligonucleotide as described for the DAMP linker. The CSO was replaced by Beaucage reagent to effect sulfurization (Iyer, R. P, Egan, W., Regan, J. B., and Beaucage, S. L. (1990) 3H-1,2-Benzodithiole-3-one 1,1-dioxide as an improved sulfurizing reagent in the solid-phase synthesis of oligodeoxyribonucleosides phosphorothioates. *J. Am. Chem. Soc.* 112, 1254–1255.). The sulfurization reaction was allowed 3 minutes at room temperature. To accommodate the larger synthesis scale, the amount of linker and tetrazole used for the reaction was increased to 0.92 mL of each reagent (20 eqs.).

After the linker modified support-bound oligonucleotide was washed and dried, the beads were added to a vial containing 10 eq. of 1-octadecylamine (stearylamine) dissolved in 2 mL of dichloromethane with 10% triethylamine. The reaction was allowed 4 hours at room temperature with continuous mixing. The beads were then washed well with dichloromethane and dried.

The oligonucleotide conjugate was then deprotected and cleaved from support using concentrated ammonium hydroxide for 5 hours at 65° C., after which time the reagent was decanted and the beads rinsed with 4 mL of 25% acetonitrile in water.

Figure 4:
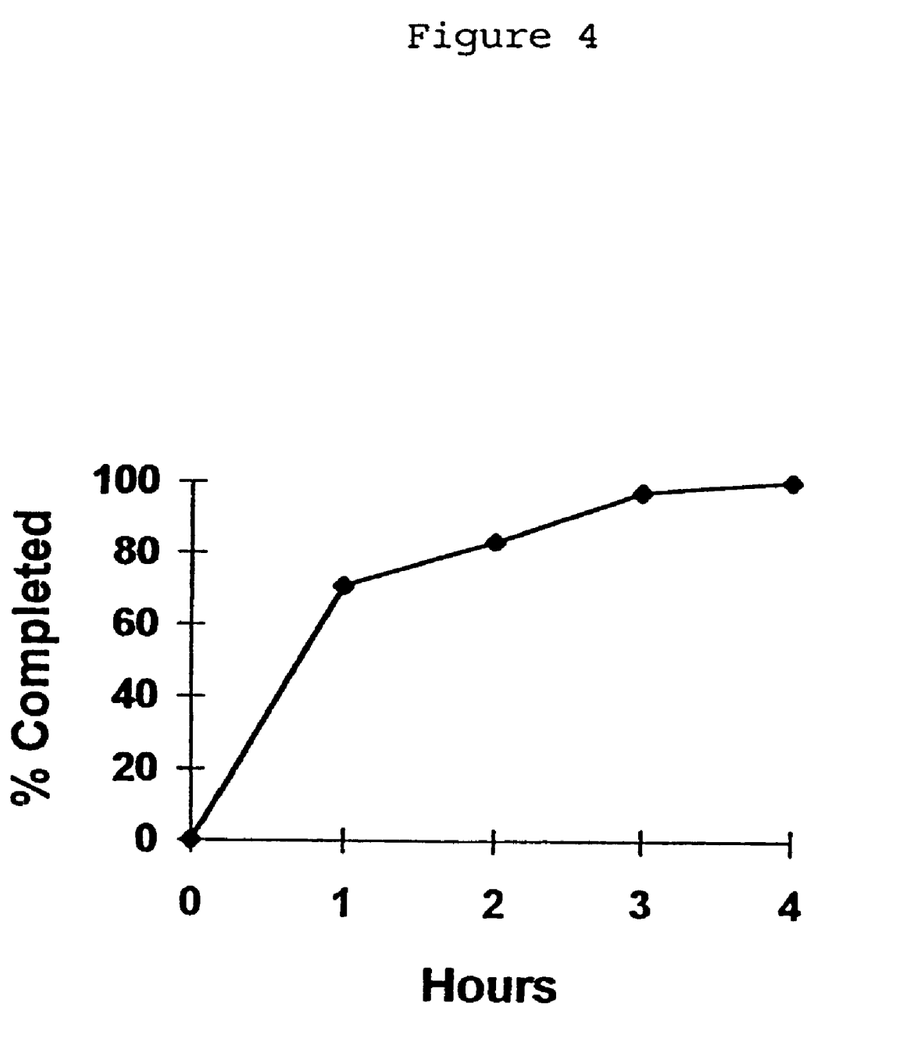
FIG. 4. Chromatogram of the crude product mixture of an octadecyl modified phosphorothioate prepared with DADE.

The crude product was analyzed and purified on a reverse-phase HPLC column as described in Methods. The product had a retention time of 40.2 minutes (52% integrated area), whereas the starting oligonucleotide had a retention of 16 minutes and the DADE modified, but unconjugated, product eluted at 18.2 minutes (FIG. 4). A total of 435 $OD_{260}$ unites of product was isolated from 965 $OD_{260}$ units of crude material (45%; 86% recovery of available product).

This oligodeoxynucleotide conjugate was found to be efficacious in reducing the clearance rates of a phosphorothioate in vivo using healthy mice (Personal communication, Mark Dizik, Genta, Inc., San Diego, Calif. 1994.).

Example 13

Use of DADE-PE to Prepare a Fluorscien Conjugate of a Phosphorothioate Oligonucleotide

The utility of the DADE-PE version of the linker (as the succinimidyl ester) was demonstrated by the preparation of an fluorescien-cadaverine conjugate to 1.0 μmole of phosphorothioate oligodeoxynucleotide. The DADE-PE linker was coupled to the support-bound phosphorothioate oligonucleotide as described for the DADE-SE linker. After the linker modified support-bound oligonucleotide was washed and dried, and reacted with 10 equivalents of fluorescien-cadaverine dissolved in 2 mL of dimethylformamide with 10% triethylamine. The reagent was pushed back and force into the column using two syringes. The reaction was allowed 1 hour at room temperature with occasional mixing. The beads were then washed well with dichloromethane and dried.

The oligonucleotide conjugate was then deprotected and cleaved from support using concentrated ammonium hydroxide for 18 hours at 55° C., after which time the reagent was decanted and the beads rinsed with 4 mL of 25% acetonitrile in water.

The crude product was analyzed by polyacrylamide gel electrophoresis ("PAGE") analysis and quantified by reverse-phase HPLC column as described in Methods. The product had a retention time of 40.2 minutes (52% integrated area), whereas the starting oligonucleotide had a retention of 12.4 minutes and the DADE modified, but unconjugated, product eluted at 18.2 minutes (FIG. 4).

We claim:

1. A composition of the formula, wherein $R_1$ is $R_2$ is

$R_3$ is —$CH_3$, —O—$CH_2$—$CH_2$—CN or —O—$CH_3$;

$R_4$ is o-chlorophenyl, β-cyanoethyl;

$X_1$ is O, S or Se; and n is 5 to 15.

2. A composition of the formula, wherein $R_1$ is $R_2$ is —$CH_3$, —O—$CH_2$—$CH_2$—CN or —O—$CH_3$;

X is O, S or Se; and n is 5 to 15.

3. A composition according to claim 1 further comprising a nucleic acid.

4. A composition according to claim 3 wherein said nucleic acid is about 1 to about 1,000 nucleotides in length.

5. A composition according to claim 3 wherein said nucleic acid is bound to a support matrix.

6. A composition according to claim 1 further comprising a support matrix.

7. A composition according to claim 1 of the formula

8. A composition according to claim 1 of the formula

9. A composition according to claim 1 of the formula

10. A composition according to claim 1 of the formula

11. A composition according to claim 1 of the formula

12. A composition according to claim 1 of the formula

13. A composition according to claim 1 of the formula

14. A composition according to claim 1 of the formula

15. A composition according to claim 1 of the formula

16. A composition of the formula, wherein
$R_5$ is a reporter group, a biomolecule, an organic molecule, or a nucleic acid not less than 1 nucleotide in length and a nucleic acid not more than 1,000 nucleotides in length;
$R_6$ is a nucleic acid not less than 1 nucleotide in length and a nucleic acid not more than 1,000 nucleotides in length;
$X_1$ is O, S, or Se; and
n is a number not less than 5 and a number not more than 15.

17. A composition of the formula, wherein
$R_5$ is a reporter group, a biomolecule, an organic molecule, or a nucleic acid not less than 1 nucleotide in length and a nucleic acid not more than 1,000 nucleotides in length;
$R_6$ is a nucleic acid not less than 1 nucleotide in length and a nucleic acid not more than 1,000 nucleotides in length;
$X_1$ is O, S, or Se; and
n is a number not less than 5 and a number not more than 15.

18. A composition according to claim 16 wherein said reporter group is selected from the group consisting of fluorescent, bioluminescent, chemiluminescent, colorimetric and radioactive agents.

19. A composition according to claim 18 wherein said fluorescent reporter group is selected from the group consisting of fluorescein, pyrene, 7-methoxycoumarin, Cascade Blue™, AMCA-X, dialkylaminocoumarin, Pacific Blue, Marina Blue, BODIPY 493/503™, BODIPY Fl-X™, DTAF, Oregon Green 500™, Dansyl-X, 6-FAM, Oregon Green 488™, Oregon Green 514™, Rhodamine Green-X™, Rhodol Green™, NBD, TET, 2', 4', 5', 7' tetrabromosulfonefluorescien, BODIPY-R6G, BODIPY-Fl Br$_2$, BODIPY 530/550™, HEX, BODIPY 558/568™, BODIPY-TMR-X™, PyMPO, BODIPY 564/570™, TAMRA, BODIPY 576/589™, Cy3™, Rhodamine Red-x, BODIPY 581/591™, carboxyXrhodamine™, Texas Red-X, BODIPY-TR-X™, Cy5™, and naphthofluorescein.

20. A composition according to claim 16 wherein said biomolecule is a protein or a peptide.

21. A composition according to claim 16 wherein said nucleic acid is a deoxyribonucleotide or a ribonucleotide.

22. A composition according to claim 17 wherein said reporter group is selected from the group consisting of fluorescent, bioluminescent, chemiluminescent, colorimetric and radioactive agents.

23. A composition according to claim 22 wherein said fluorescent reporter group is selected from the group consisting of fluorescein, pyrene, 7-methoxycoumarin, Cascade Blue™, AMCA-X, dialkylaminocoumarin, Pacific Blue, Marina Blue, BODIPY 493/503™, BODIPY Fl-X™, DTAF, Oregon Green 500™, Dansyl-X, 6-FAM, Oregon Green 488™, Oregon Green 514™, Rhodamine Green-X™, Rhodol Green™, NBD, TET, 2', 4', 5', 7' tetrabromosulfonefluorescien, BODIPY-R6G, BODIPY-Fl Br$_2$, BODIPY 530/550™, HEX, BODIPY 558/568™, BODIPY-TMR-X™, PyMPO, BODIPY 564/570™, TAMRA, BODIPY 576/589™, Cy3™, Rhodamine Red-x, BODIPY 581/591™, carboxyXrhodamine™, Texas Red-X, BODIPY-TR-X™, Cy5™, and naphthofluorescein.

24. A composition according to claim 17 wherein said biomolecule is a protein or a peptide.

25. A composition according to claim 17 wherein said nucleic acid is a deoxyribonucleotide or a ribonucleotide.

* * * * *